United States Patent
Ohya (10) Patent No.: US 8,441,357 B2
(45) Date of Patent: May 14, 2013

(54) ALCOHOL CONCENTRATION DETECTING DEVICE

(75) Inventor: Naoshi Ohya, Chiryu (JP)

(73) Assignee: Denso Corporation, Kariya (JP)

( * ) Notice: Subject to any disclaimer, the term of this patent is extended or adjusted under 35 U.S.C. 154(b) by 288 days.

(21) Appl. No.: 12/925,883

(22) Filed: Nov. 1, 2010

(65) Prior Publication Data

US 2011/0102182 A1 May 5, 2011

(30) Foreign Application Priority Data

Nov. 2, 2009 (JP) ................................. 2009-251941

(51) Int. Cl.
*G08B 23/00* (2006.01)

(52) U.S. Cl.
USPC ............... 340/576; 340/691.6; 340/825.36

(58) Field of Classification Search .......... 340/576, 340/571, 632, 870.09, 870.17, 691.6, 825.36
See application file for complete search history.

(56) References Cited

U.S. PATENT DOCUMENTS

| | | | |
|---|---|---|---|
| 4,749,553 A * | 6/1988 | Lopez et al. | 422/84 |
| 5,305,613 A | 4/1994 | Hotta et al. | |
| 5,495,744 A * | 3/1996 | Ueda et al. | 73/1.07 |
| 5,524,446 A | 6/1996 | Hotta et al. | |
| 5,572,881 A | 11/1996 | Hotta et al. | |
| 6,622,924 B2 | 9/2003 | Arata | |
| 7,095,501 B2 * | 8/2006 | Lambert et al. | 356/439 |
| 7,377,186 B2 * | 5/2008 | Duval | 73/863.01 |
| 7,690,421 B2 | 4/2010 | Burns et al. | |
| 2003/0019223 A1 | 1/2003 | Arata et al. | |
| 2009/0043409 A1 * | 2/2009 | Ota | 700/90 |
| 2010/0043524 A1 * | 2/2010 | Takata | 73/23.3 |
| 2010/0140366 A1 | 6/2010 | Burns et al. | |
| 2010/0297925 A1 | 11/2010 | Burns et al. | |

FOREIGN PATENT DOCUMENTS

| | | |
|---|---|---|
| JP | 60-100749 | 6/1985 |
| JP | 05-147500 | 6/1993 |
| JP | 6-148107 | 5/1994 |
| JP | 07-120463 | 5/1995 |
| JP | 7-120463 | 5/1995 |
| JP | 8-145928 | 6/1996 |
| JP | 2002-277425 | 9/2002 |
| JP | 2004-212217 | 7/2004 |
| JP | 2007-106277 | 4/2007 |
| JP | 2009-37563 | 2/2009 |
| JP | 2009-040403 | 2/2009 |
| JP | 2009-042166 | 2/2009 |
| JP | 2009-174937 | 8/2009 |
| JP | 2009-198373 | 9/2009 |
| JP | 2009-229307 | 10/2009 |

OTHER PUBLICATIONS

Office action date Oct. 4, 2011 in corresponding Japanese Application No. 2009-251941.

* cited by examiner

*Primary Examiner* — Danile Previl
(74) *Attorney, Agent, or Firm* — Harness, Dickey & Pierce, PLC (57) ABSTRACT

An alcohol concentration detecting device for a vehicle includes an alcohol sensor to detect alcohol component contained in an expiration of an occupant of the vehicle, a gas sensor to detect gas components other than the alcohol component contained in the expiration, and a controller to calculate alcohol concentration based on detection value of the alcohol sensor. The controller corrects the calculated alcohol concentration based on detection value of the gas sensor. The alcohol sensor and the gas sensor are configured to further detect a state of air in a passenger compartment of the vehicle.

6 Claims, 8 Drawing Sheets

|  | AIR | EXPIRATION |
|---|---|---|
| $O_2$ | 20.6% | 15.2% |
| $CO_2$ | 0.03% | 5% |
| $H_2O$ | VARIED | VARIED BY EXPIRATION DEPTH OR TEMPERATURE |

ALCOHOL CONCENTRATION DETECTING DEVICE

CROSS REFERENCE TO RELATED APPLICATION

This application is based on Japanese Patent Application No. 2009-251941 filed on Nov. 2, 2009, the disclosure of which is incorporated herein by reference in its entirety.

BACKGROUND OF THE INVENTION

1. Field of the Invention

The present invention relates to an alcohol concentration detecting device.

2. Description of Related Art

JP-A-2009-37563 describes an alcohol concentration detecting device used for preventing a drunken driving. The device detects alcohol concentration contained in expiration of a car driver, and prohibits an engine from being started when the detected alcohol concentration is equal to or higher than a predetermined value.

JP-B-4208871 describes an alcohol concentration detecting device. The device includes plural sensors to react alcohol other than ethyl alcohol, and calculates alcohol concentration based on detection values of the plural sensors so as to raise detection accuracy of the alcohol concentration.

A variety of sensors are mounted in a passenger compartment of a vehicle, and monitor environmental air state in the passenger compartment. For example, an air-conditioning device has a sensor to detect a temperature or humidity in the passenger compartment, and controls air-conditioning in a manner that the passenger compartment has a temperature set by an occupant of the vehicle. Function of this sensor may overlap with that of the sensor of JP-B-4208871. In this case, sensor mounting condition may not be the best as a whole of the vehicle.

SUMMARY OF THE INVENTION

In view of the foregoing and other problems, it is an object of the present invention to provide an alcohol concentration detecting device.

According to an example of the present invention, an alcohol concentration detecting device for a vehicle includes an alcohol sensor to detect alcohol component contained in an expiration of an occupant of the vehicle, a gas sensor to detect gas components other than the alcohol component contained in the expiration, and an alcohol-detecting controller to calculate alcohol concentration based on detection value of the alcohol sensor. The alcohol-detecting controller corrects the calculated alcohol concentration based on detection value of the gas sensor. The alcohol sensor and the gas sensor are configured to further detect a state of air in a passenger compartment of the vehicle.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF PREFERRED EMBODIMENT

First Embodiment

An alcohol concentration detecting device 10 is used for preventing a drunken driving, and is mounted in a passenger compartment of a vehicle, for example.

Figure 1:
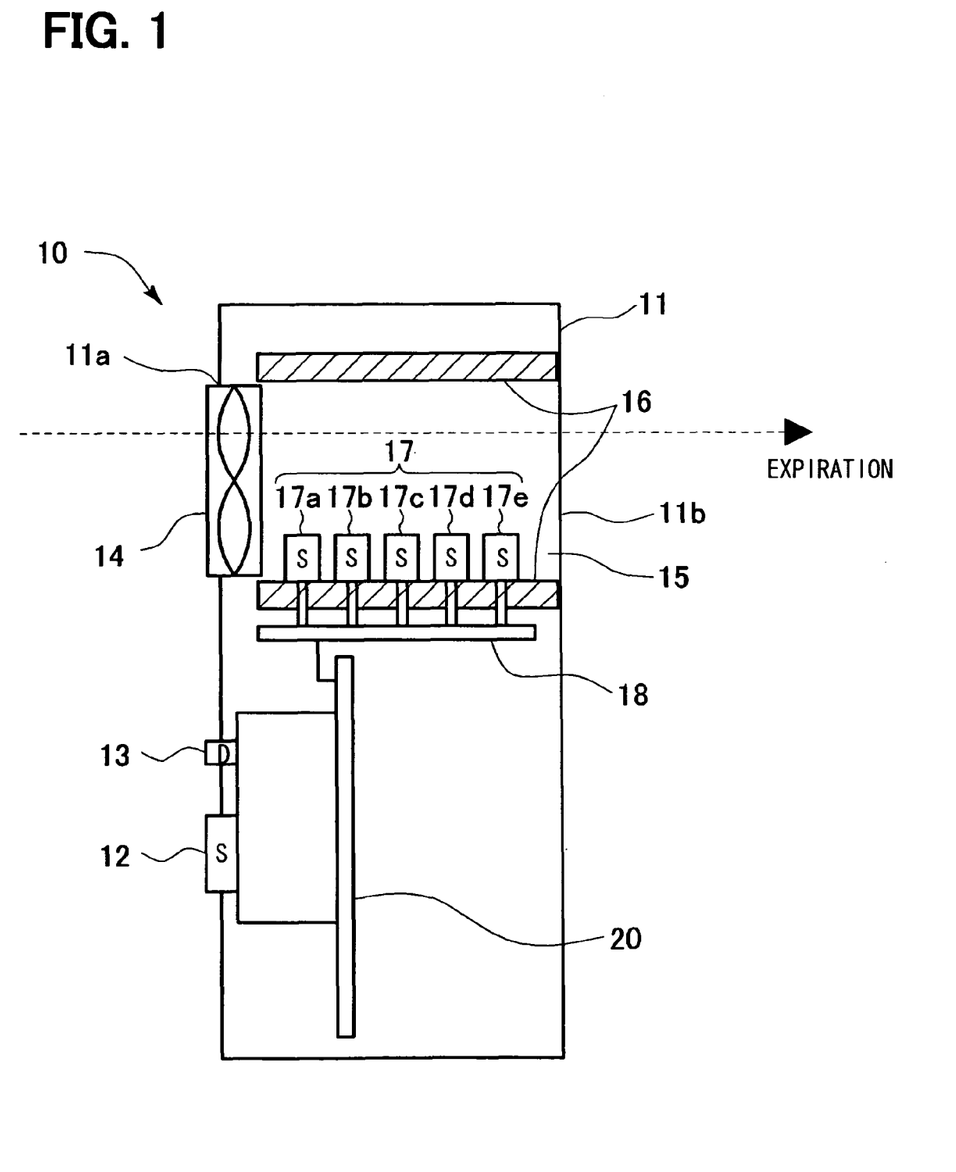
FIG. 1 is a schematic view illustrating an alcohol concentration detecting device according to a first embodiment.

The alcohol concentration detecting device 10 will be described with reference to FIG. 1. The alcohol concentration detecting device 10 is arranged near a driver's seat of the vehicle, for example, in a manner that the driver easily operates the device 10. The device 10 has a case 11, an operation switch 12, a display portion 13, a fan 14, an expiration passage 15, an inner wall 16, plural gas sensors 17, and an alcohol-detecting electronic control unit (ECU) 20.

The case 11 has an inlet 11a from which a driver's expiration is taken into the case 11, and an outlet 11b for discharging the expiration out of the case 11. The driver grips the case 11 and blows expiration into the inlet 11a from a mouth of the driver. At this time, the expiration flows towards the outlet 11b through the expiration passage 15 inside of the inner wall 16.

When the expiration or air in the passenger compartment is taken into the case 11 through the inlet 11a, the operation switch 12 is turned on. The operation switch 12 is arranged at a front of the case 11, and is protruded outward from the case 11.

The display portion 13 has plural, for example, three LEDs, and detection result of the device 10 is displayed on the display portion 13. The display portion 13 is arranged on a front face of the case 11 in a manner that the driver can see a state of the display portion 13 from outside. For example, all the LEDs of the display portion 13 blink when the alcohol concentration is equal to or higher than a predetermined value. For example, all the LEDs of the display portion 13 is maintained to light when the alcohol concentration is lower than the predetermined value.

The fan 14 is arranged to cover the whole region of the inlet 11a, and is driven by a drive signal output from the ECU 20 when the operation switch 12 is turned on. At this time, expiration or air in the passenger compartment is compulsorily drawn toward the gas sensors 17 through the inlet 11a. Due to the fan 14, the expiration or air in the passenger compartment flows through the expiration passage 15 in an agitated state. Therefore, the expiration or air in the passenger compartment equally contacts each of the sensors 17. The fan 14 may correspond to an expiration drawing portion of the present invention.

The gas sensors 17 are mounted to a substrate 18, and are projected into the expiration passage 15. The gas sensors 17 are constructed by an alcohol sensor 17a, an odor sensor 17b, a temperature sensor 17c, a humidity sensor 17d, and an oxygen sensor 17e, for example.

Figure 3:
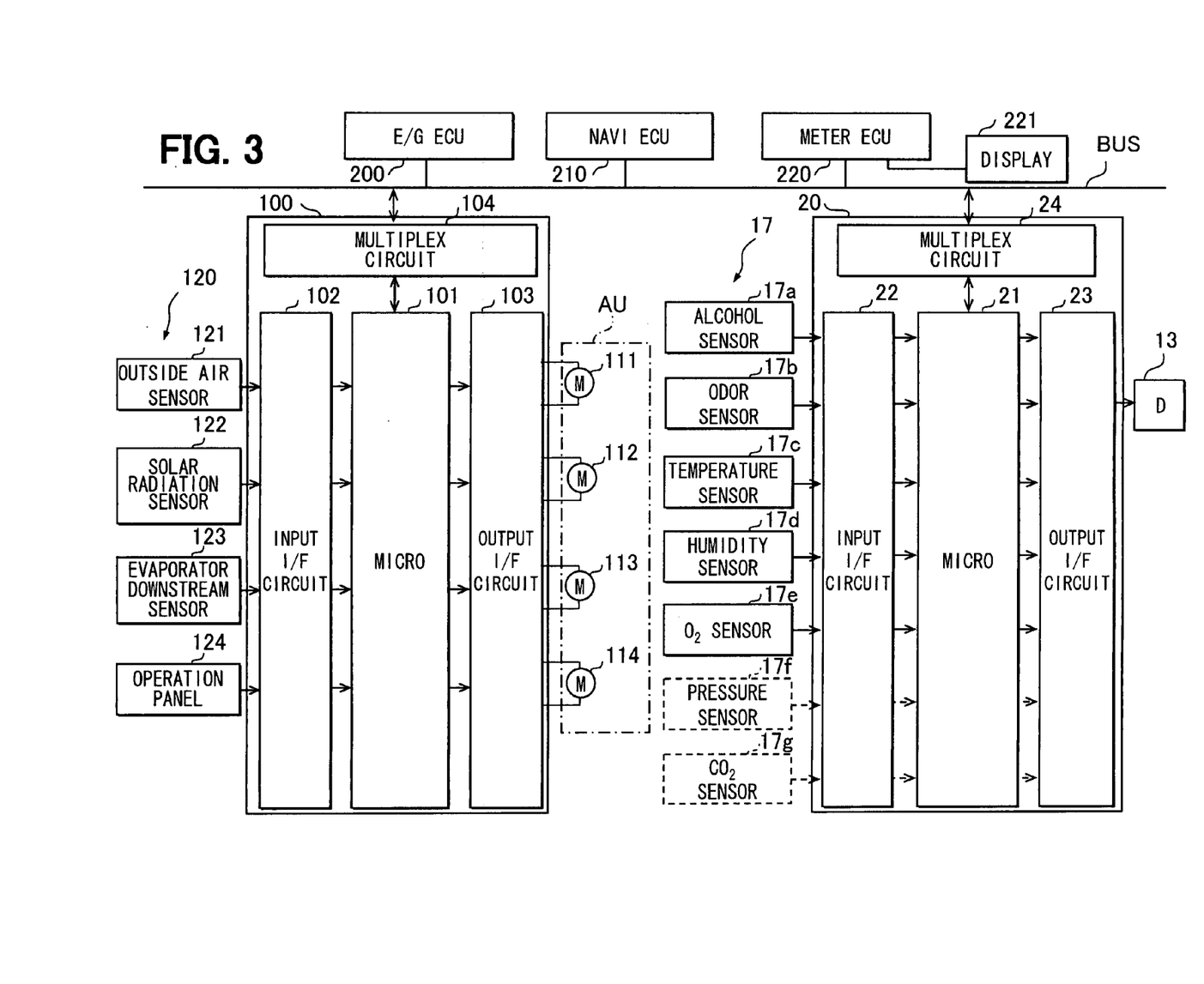
FIG. 3 is a block diagram illustrating an alcohol-detecting ECU of the alcohol concentration detecting device.

As shown in FIG. 3, the alcohol-detecting ECU 20 mainly includes a microcomputer 21 having CPU, ROM and RAM, an input interface (I/F) circuit 22, and an output I/F circuit 23. The microcomputer 21 obtains detection values of the gas sensors 17 through the input I/F circuit 23, and executes an alcohol concentration calculation program of FIG. 6 and an air purity calculation program of FIG. 7, which are memorized in the ROM in advance, based on the detection values. The microcomputer 21 outputs a control signal into the output I/F circuit 23 based on the execution result. The microcomputer 21 of the alcohol-detecting ECU 20 may correspond to an alcohol-detecting controller of the present invention.

The alcohol-detecting ECU 20 has a multiplex communication circuit 24. The multiplex communication circuit 24 of the ECU 20 is connected to an air-conditioning ECU 100, an engine ECU 200, a navigation ECU 210, and a meter ECU 220 through a multiplex communication line BUS such as CAN or LIN, so that two-way communication is possible.

An air-conditioner is defined by the air-conditioning ECU 100 and an air-conditioning unit AU. The air-conditioning ECU 100 includes a microcomputer 101 having CPU, ROM and RAM, an input I/F circuit 102, and an output I/F circuit 103, similar to the alcohol-detecting ECU 20. The microcomputer 101 executes a temperature control program or air inlet switch program (not shown) memorized in the ROM in advance. The microcomputer 101 outputs a control signal into the output I/F circuit 103 based on the execution result. The output I/F circuit 103 includes a drive circuit, and a drive signal is output into a blower motor 111, an air inlet changing damper motor 112, an air mixing damper motor 113, or an air outlet mode changing damper motor 114 of the unit AU based on the signal output from the microcomputer 101. Air-conditioning sensors 120 are connected to the input I/F circuit 102. The microcomputer 101 of the air-conditioning ECU 100 may correspond to an air-conditioning controller of the present invention.

The air-conditioning sensors 120 are constructed by an outside air sensor 121, a solar radiation sensor 122, and an evaporator downstream sensor 123. The outside air sensor 121 detects an outside air temperature, and outputs the detection value into the input I/F circuit 102. The solar radiation sensor 122 detects an amount of solar radiation, and outputs the detection value into the input I/F circuit 102. The evaporator downstream sensor 123 detects a temperature of air immediately after passing through an evaporator, and outputs the detection value into the input I/F circuit 102.

An operation panel 124 is connected to the air-conditioning ECU 100, and has various switches. For example, a blower control switch is used for changing an amount of air sent by the blower motor 111. An air inlet changing switch is used for operating the inlet changing damper motor 112 corresponding to an air inlet switching portion. A temperature control switch is used for setting a temperature, that is, for operating the air mixing damper motor 113. An air outlet changing switch is used for operating the outlet mode switching damper motor 114. An automatic mode switch is used for setting a full-automatic mode. An air-conditioning switch is used for turning on/off a magnet clutch of a compressor, so as to open/close a refrigerant passage extending toward the evaporator. The operation panel 124 has a display such as liquid crystal display (LCD) for displaying the mode and the temperature set by the above switches.

The air-conditioning ECU 100 has a multiplex communication circuit 104 for multiplex communication. The circuit 104 of the ECU 100 is connected to the alcohol-detecting ECU 20 through the multiplex communication line BUS, thereby two-way communication is possible.

The air-conditioning ECU 100 receives detection values from the temperature sensor 17c and the humidity sensor 17d connected to the alcohol-detecting ECU 20 through the multiplex communication line BUS. The air-conditioning ECU 100 receives a control signal from the ECU 20 through the multiplex communication line BUS, so that the air-conditioning unit AU is switched to have an outside air introduction mode, for example, based on the control signal.

The engine ECU 200 prohibits the engine from being started based on information about the alcohol concentration transmitted from the alcohol-detecting ECU 20. For example, the information represents a determination result that the alcohol concentration is equal to or higher than a predetermined value.

The meter ECU 220 has a display 221 to display information such as temperature and humidity based on the detection values of the temperature sensor 17c and the humidity sensor 17d. Alternatively, the information may be the alcohol concentration and the air purity of the passenger compartment sent from the ECU 20.

The display 221 is made of a liquid crystal display (LCD), for example, and is arranged on a meter panel having various meters such as velocity meter or engine rotation number meter, in front of the driver's seat. The display 221 displays a message of engine activation impossible when the alcohol concentration is equal to or higher than the predetermined value, because the driver is drunken. The display 221 displays a message of engine activation possible when the alcohol concentration is lower than the predetermined value, because the driver is not drunken. Moreover, the display 221 displays information about temperature, humidity and air purity transmitted from the alcohol-detecting ECU 20. The display 221 may correspond to an alarm portion of the present invention.

The alcohol sensor 17a is a semiconductor sensor to detect alcohol component contained in a driver's expiration, and outputs a sensor resistance as the detection value. Specifically, as show in FIG. 2, the alcohol sensor 17a is produced by sintering a surface of metal oxide 17a1 such as tin oxide. A coil 17a2 made of platinum is arranged on the alcohol sensor 17a overlapping with the metal oxide 17a1. A detector circuit 17a3 is connected to the metal oxide 17a1, and a power supply circuit 17a4 is connected to the coil 17a2. The metal oxide 17a1 is heated to have a predetermined temperature when the coil 17a2 receives electricity periodically from the power supply circuit 17a4. Steam and foreign matter adhering to the surface of the metal oxide 17a1 are removed periodically by the periodical electricity supplying.

Figure 2:
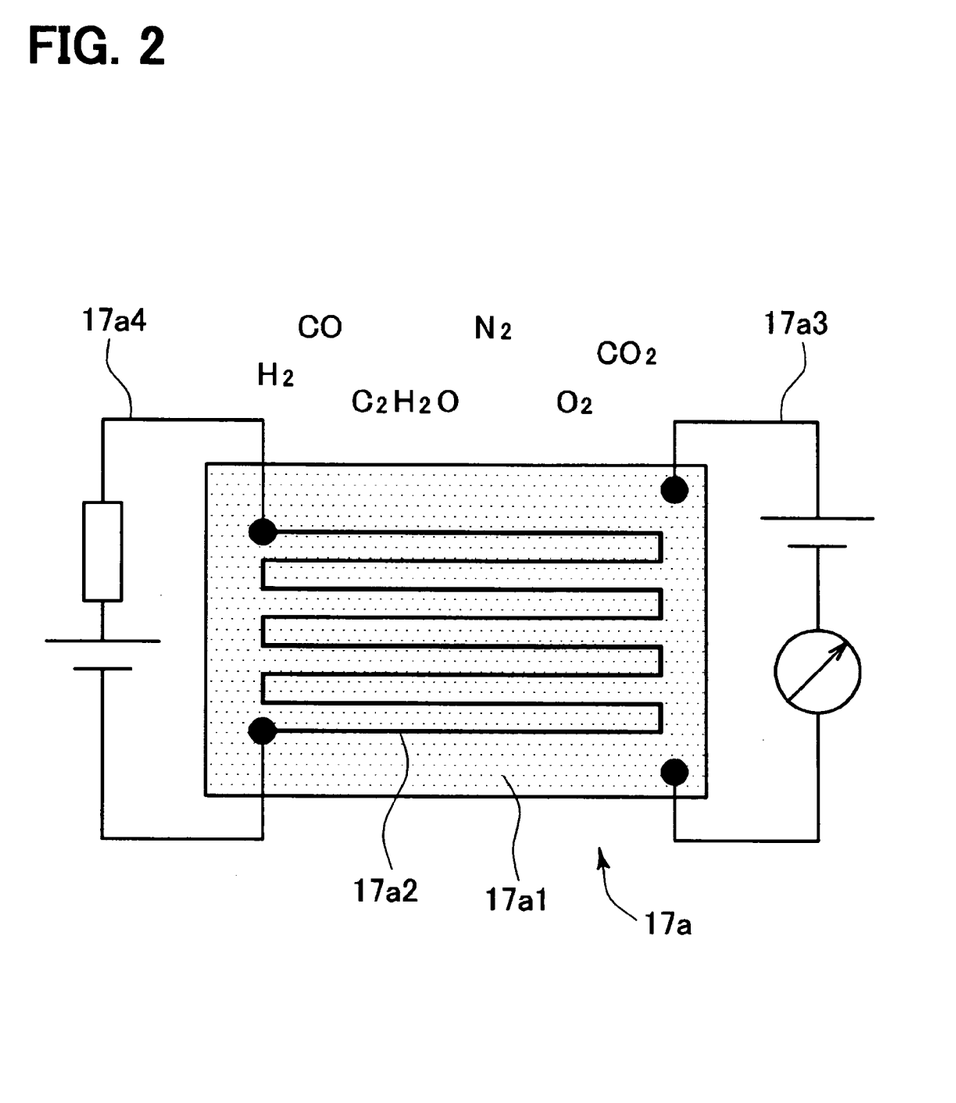
FIG. 2 is a schematic view illustrating an alcohol sensor of the alcohol concentration detecting device.

Operation of the alcohol sensor 17a will be explained briefly.

An alcohol component is not included or very few in atmospheric air. Because oxygen atom in the atmospheric air and electron in the metal oxide 17a1 are combined with each other, current is difficult to flow through the metal oxide 17a1. In contrast, when expiration containing alcohol component contacts the metal oxide 17a1, the alcohol component reacts with the oxygen atom, so that the oxygen atom is separated from the electron in the metal oxide 17a1. That is, the electron in the metal oxide 17a1 becomes free, and current can flow through the metal oxide 17a1. This reaction is detected by the detector circuit 17a3. The alcohol concentration in the expiration is measured by measuring the change of sensor resistance of the metal oxide 17a1.

The sensor resistance of the alcohol sensor 17a may change in response to odor gas component other than the alcohol component, and the odor sensor 17b is used for eliminating the influence of the other odor gas component. The odor sensor 17b is made of a semiconductor element similar to the alcohol sensor 17a, and detects a disturbance gas to affect the sensor resistance of the alcohol sensor 17a. The disturbance gas corresponds to the other odor gas component. The odor sensor 17b outputs a sensor resistance as the detection value, and has approximately the same construction as the alcohol sensor 17a of FIG. 2.

The temperature sensor 17c is a semiconductor sensor corresponding to a thermistor, for example, made of oxide of nickel, cobalt or manganese. A temperature of the expiration is changed by a way to blow the expiration by the driver. For example, when the expiration arises from a body inside of the driver such as lung, the temperature is high, and it is easy to judge the expiration to contain the alcohol component or not. In contrast, the temperature is low, when the expiration arises from a mouth of the driver, or when the expiration is a fraud one generated by using air in a balloon, for example. Moreover, the temperature of the expiration is changed by outside air temperature. For this reason, the expiration is judged to arise from the driver's lung or not by monitoring the change of the temperature detected by the temperature sensor 17c.

The humidity sensor 17d measures air humidity based on a capacitance change, for example, because conductivity and electrostatic capacitance of a sensor element is changed by a moisture content in air. The alcohol sensor 17a may react with the air humidity. That is, the alcohol sensor 17a may erroneously react, even if the driver is not drunken. Even when the alcohol sensor 17a erroneously reacts the air humidity or usual-level alcohol component in the expiration, the detection value is not adopted by monitoring the change of the humidity detected by the humidity sensor 17d.

The oxygen sensor 17e detects oxygen concentration of the expiration diluted by mixing with air in the passenger compartment. The oxygen sensor 17e may be made of a semiconductor sensor similar to the alcohol sensor 17a. Oxygen concentration of the air in the passenger compartment is almost constant even if weather or occupant number is changed. The oxygen concentration in the expiration is lower than the atmospheric oxygen concentration when the expiration is diluted by the atmospheric air. Therefore, a dilution ratio of the expiration can be judged by monitoring the change of the oxygen concentration detected by the oxygen sensor 17e.

When the expiration blown by the driver is diluted by the atmospheric air, the oxygen sensor 17e computes the dilution ratio. The dilution ratio is used for correcting the calculated alcohol concentration. The correction of the alcohol concentration using the oxygen sensor 17e will be explained below.

The expiration blown by the driver will be drawn into the alcohol concentration detecting device 10. At the same time, atmospheric air in the passenger compartment is also drawn into the device 10. Because the expiration is diluted by the atmospheric air, the alcohol concentration calculated based on the sensor resistance of the alcohol sensor 17a becomes smaller than an actual alcohol concentration. Therefore, the dilution ratio of the expiration is calculated, and the alcohol concentration is corrected based on the dilution ratio.

Figure 4:
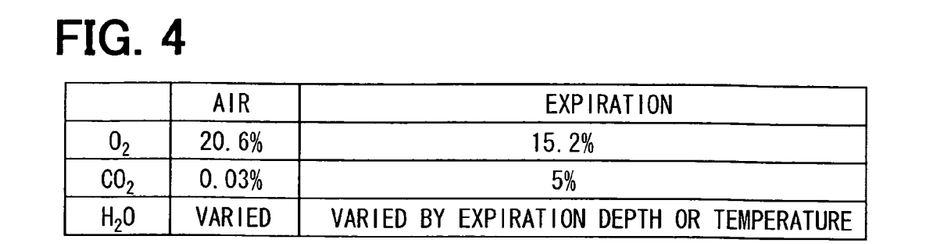
FIG. 4 is a view illustrating a gas component ratio in atmospheric air and a gas component ratio in expiration.

As shown in FIG. 4, oxygen concentration is about 20.6% and carbon dioxide concentration is about 0.03% in the atmospheric air. A moisture content such as steam is varied by humidity or temperature.

In contrast, oxygen concentration is about 15.2% and carbon dioxide concentration is about 5% in the expiration not diluted by the atmospheric air. A moisture content is varied by expiration depth or temperature. That is, each gas concentration differs between the atmospheric air and the expiration. The dilution ratio can be calculated by measuring each gas concentration in expiration-air mixture drawn into the device 10.

Because the oxygen concentration is high and stable in both of the atmospheric air and the expiration, the dilution ratio can be properly calculated by comparing the oxygen concentrations. If the oxygen concentration of the expiration-air mixture drawn into the alcohol concentration detecting device 10 is assumed as 15.2%, for example, the mixture is determined not to have dilution, because the oxygen concentration is equal to that in the expiration not having a dilution.

Figure 5:
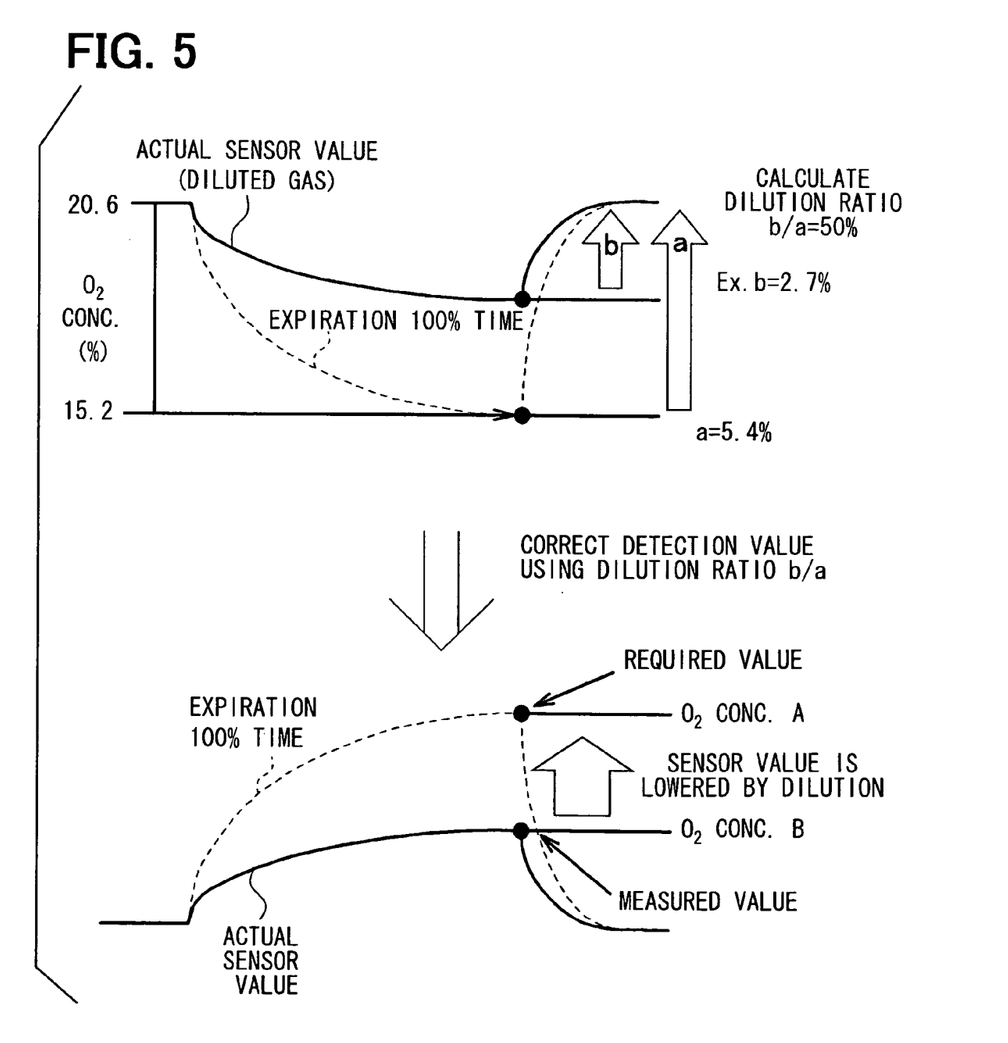
FIG. 5 is an explanatory view illustrating a method of calculating a dilution ratio performed by the ECU.

As shown in FIG. 5, the oxygen sensor 17e measures the oxygen concentration of the expiration-air mixture, and calculates a difference b (=2.7% in FIG. 5) between the measured oxygen concentration and the oxygen concentration in the atmospheric air (e.x., 20.6%).

If there is no dilution, a difference a (=5.4%) is defined between the oxygen concentration in the atmospheric air (e.x., 20.6%) and the oxygen concentration in the expiration (e.x., 15.2%). The dilution ratio is calculated by a formula of b/a. In the example of FIG. 5, the dilution rate (b/a) is 50%. The alcohol concentration can be corrected by dividing the computed alcohol concentration by the dilution ratio (b/a).

The influence of the disturbance gas is eliminated based on the detection value of the odor sensor 17b. Further, air mixed into the expiration is eliminated based on the detection values of the temperature sensor 17c and the humidity sensor 17d. That is, expiration drawn into the device 10 becomes suitable for detection.

Therefore, the calculated alcohol concentration has less dispersion, and almost the same value can be obtained as an actual alcohol concentration. The dilution ratio may be calculated by using the humidity of the air-expiration mixture, so that the dilution ratio may be calculated base on both of the oxygen concentration and the humidity.

Operation of the alcohol concentration detecting device 10 will be explained. The microcomputer 21 of the ECU 20 repeats and executes alcohol concentration calculation program of FIG. 6 memorized in the ROM in response to an on-signal of the operation switch 12 for every predetermined short time.

Figure 6:
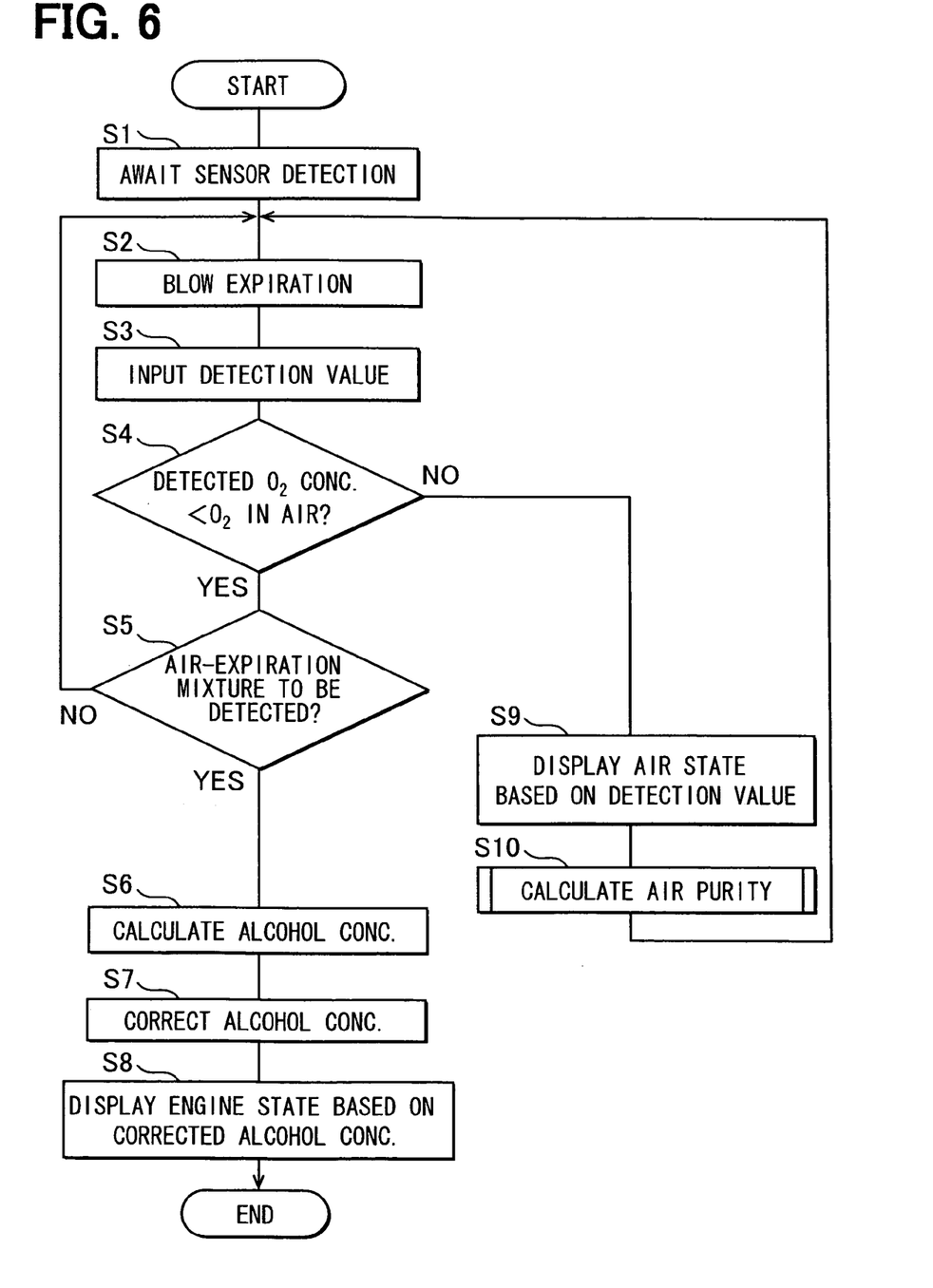
FIG. 6 is a flow chart illustrating an alcohol concentration calculation program executed by the ECU.

Alcohol concentration calculation process (S1-S8) is explained with reference to FIG. 6. Each of the sensors 17a-17e becomes to have a detection standby state when the operation switch 12 is turned on (S1). When the device 10 is used for preventing drunken driving, a driver brings own mouse close to the device 10 and blows own expiration to the inlet 11a of the case 11 (S2). The expiration is mixed with atmospheric air in the passenger compartment or air in the case 11, and the expiration-air mixture flows inside of the inner wall 16.

The mixture is agitated by the fan 14, and is sent toward downstream of the expiration passage 15. While the mixture passes through the expiration passage 15, the mixture contacts the alcohol sensor 17a, the odor sensor 17b, the temperature sensor 17c, the humidity sensor 17d, and the oxygen sensor 17e, before the mixture is discharged out of the outlet 11b. At this time, the microcomputer 21 of the ECU 20 inputs and memorizes detection values of the gas sensors 17a-17e into the RAM (S3).

If the oxygen concentration corresponding to the detection value of the oxygen sensor 17e is lower than a predetermined value (S4: Yes), the microcomputer 21 determines the mixture to contain expiration. For example, the predetermined value may be the oxygen concentration in the atmospheric air of FIG. 4.

If the mixture is determined to be suitable for detection based on the detection values of the odor sensor 17b, the temperature sensor 17c, and the humidity sensor 17d (S5: Yes), the microcomputer 21 calculates the alcohol concentration based on the detection value of the alcohol sensor 17a (S6).

The alcohol concentration is corrected by dividing the computed alcohol concentration by the dilution ratio (S7), as shown in FIG. 5. If the mixture is determined not to be suitable for the detection (S5: No), the microcomputer 21 blinks the LED of the display portion 13 so as to alarm a detection error to the driver.

The microcomputer 21 judges the driver to be drunken or not based on the corrected alcohol concentration, and reports the judgment result to the driver through the display portion 13. At the same time, the microcomputer 21 sends a message information that an engine is disabled to be started when the driver is judged to be drunken. The microcomputer 21 sends a message information that an engine is able to be started when the driver is judged not to be drunken. The message information is sent into the meter ECU 220 through the line BUS, and is displayed on the display 221 (S8).

An air state monitor process (S1-S4, S9, S10) in the passenger compartment is explained with reference to FIG. 6. In a case where the alcohol concentration detecting device 10 is used for monitoring the air state in the passenger compartment, the device 10 is activated by turning on the operation switch 12, or by receiving a request from ECU on the multiplex communication line BUS.

While air in the passenger compartment passes through the expiration passage 15 toward the outlet 11b, the air is agitated by the fan 14, and the air contacts the sensors 17a-17e. In this case, similar to a case in which the driver blows expiration into the inlet 11a of the device 10, the microcomputer 21 inputs and memorizes the detection values of the sensors 17a-17e into the RAM (S3).

However, in this case, the oxygen concentration detected by the sensor 17e is equal to or higher than the predetermined value (S4: No), thereby the microcomputer 21 performs a process of S9. The microcomputer 21 sends the temperature information detected by the temperature sensor 17c and the humidity information detected by the humidity sensor 17d into the meter ECU 220 through the line BUS, so as to display the information on the display 221 (S9).

The occupant of the vehicle can see the temperature and humidity information as one index of air state in the passenger compartment through the display 221. Moreover, these information are further transmitted to the air-conditioning ECU 100 through the multiplex communication line BUS. The air-conditioning ECU 100 controls the motor 111-114 by referring to the information output from the ECU 20 in addition to the sensor information output from the sensors 120 in a case where the operation panel 124 is on.

Figure 7:
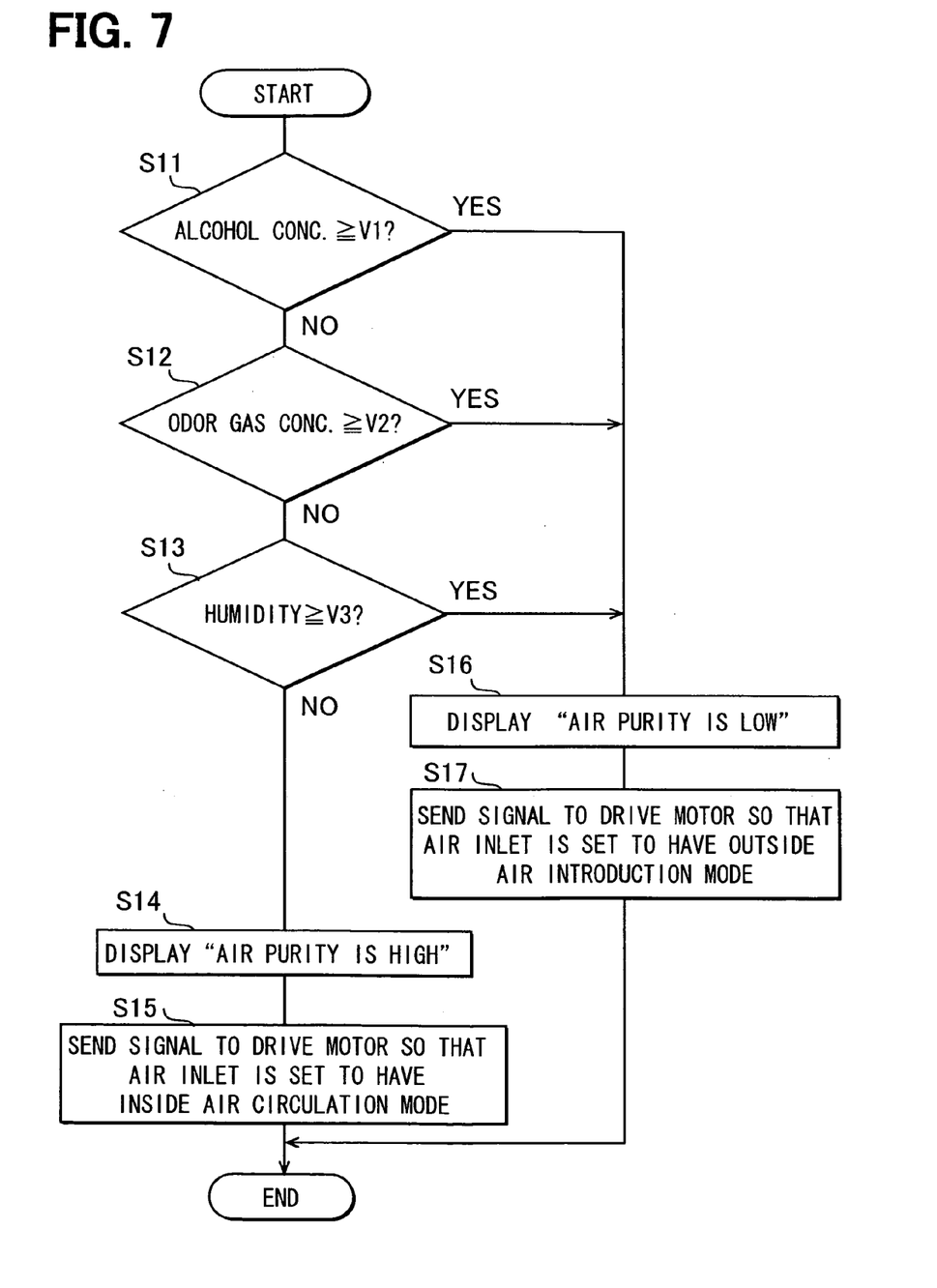
FIG. 7 is a flow chart illustrating an air purity calculation program executed in the alcohol concentration calculation program.

The microcomputer 21 performs an air purity calculation process of S10 after S9. FIG. 7 is a flow chart showing an air purity calculation routine performed in S10. In this routine, the microcomputer 21 computes alcohol concentration based on the detection value of the alcoholic sensor 17a, and judges the computed alcohol concentration to be equal to or higher than a preset value V1 (S11).

When the alcohol concentration is lower than the preset value V1 (S11: No), the odor gas concentration is computed based on the detection value of the odor sensor 17b, and the calculated odor gas concentration is determined to be equal to or higher than a preset value V2 (S12).

When the odor gas concentration is lower than the value V2 (S12: No), the humidity is computed based on the detection value of the humidity sensor 17d, and the computed humidity is determined to be equal to or higher than a preset value V3 (S13). The process of S11-S13 performed by the microcomputer 21 may correspond to an air purity calculator of the present invention.

Figure 8A:
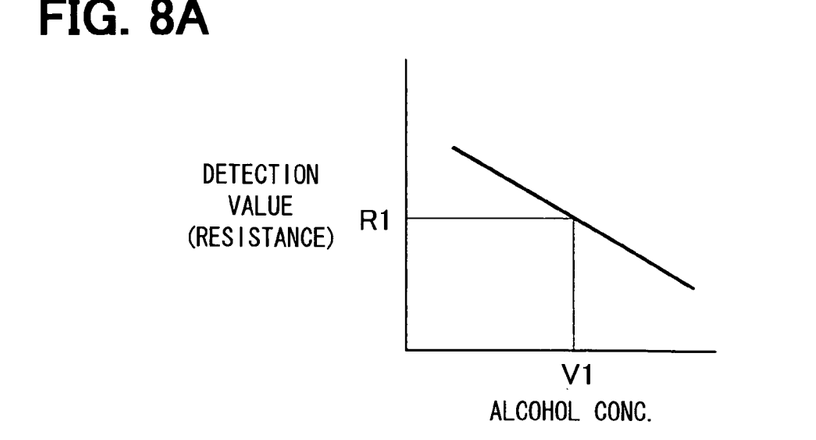
FIG. 8A is a judgment table illustrating a relationship between alcohol concentration and detection value of the alcohol sensor.
Figure 8B:
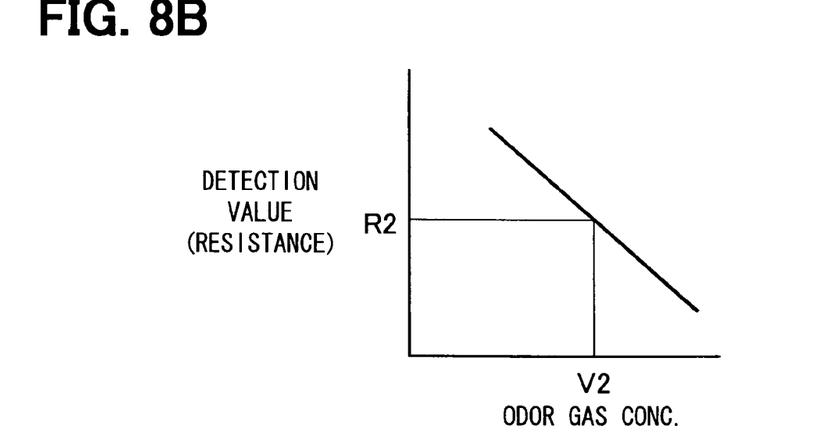
FIG. 8B is a judgment table illustrating a relationship between odor gas concentration and detection value of odor sensor.
Figure 8C:
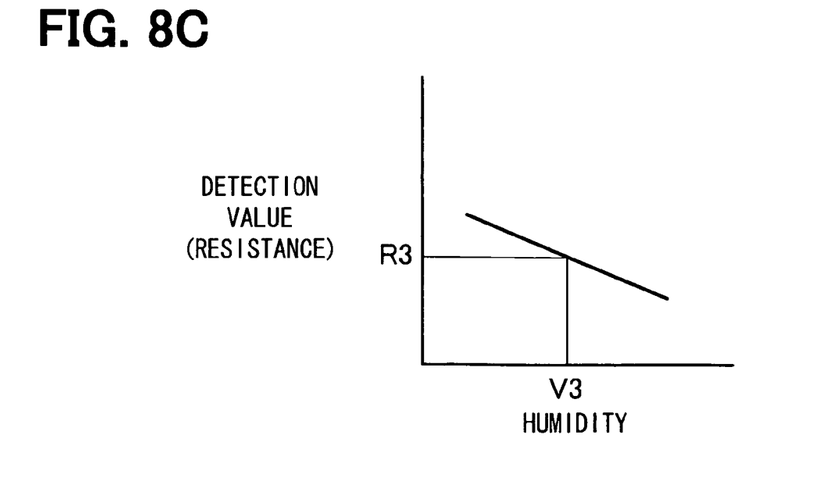
FIG. 8C is a judgment table illustrating a relationship between humidity and detection value of humidity sensor.

The process of S11-S13 may be performed based on a predetermined formula. For example, the process may be executed by referring to a judgment table in which each detection value and gas concentration have a predetermined relationship as shown in FIGS. 8A, 8B and 8C.

When the microcomputer 21 determines at least one of the alcohol concentration, the odor gas concentration and the humidity to be equal to or higher than the preset value (at least one of S11, S12 and S13 is Yes), a message information that the air purity in the passenger compartment is low is transmitted to the meter ECU 220 through the multiplex communication line BUS, and is displayed on the display 221 (S16).

Moreover, the microcomputer 21 transmits a control signal to the air-conditioning ECU 100 so as to drive the inlet changing motor 112 in a manner that an air inlet of the air-conditioning unit AU has an outside air introduction mode (S17). Therefore, the air inlet is semi-automatically changed to have the outside air introduction mode if the operation panel 124 is turned on.

When the microcomputer 21 determines all of the alcohol concentration, the odor gas concentration and the humidity to be lower than the preset value (all of S11, S12 and S13 are No), a message information that the air purity in the passenger compartment is high is transmitted to the meter ECU 220 through the multiplex communication line BUS, and is displayed on the display 221 (S14).

Moreover, the microcomputer 21 transmits a control signal to the air-conditioning ECU 100 so as to drive the inlet changing motor 112 in a manner that the air inlet of the air-conditioning unit AU has an inside air circulation mode (S15). Therefore, the air inlet is semi-automatically changed to have the inside air circulation mode if the operation panel 124 is turned on.

The occupant is encouraged to turn on the operation panel 124 by the message information that the air purity in the passenger compartment is low. Because the air inlet is semi-automatically changed to have the outside air introduction mode, the air in the passenger compartment can be kept clean.

According to the first embodiment, the gas sensors 17 are used for detecting the air state in the passenger compartment other than for detecting the alcohol concentration which is an original use of the device 10. If a sensor mounted in other equipment has an overlapping function, the sensor can be eliminated. Therefore, sensors mounting situation can be optimized as a whole of the vehicle.

Second Embodiment

The microcomputer 21 of the alcohol-detecting ECU 20 corresponds to the air purity calculator in the first embodiment.

Figure 9:
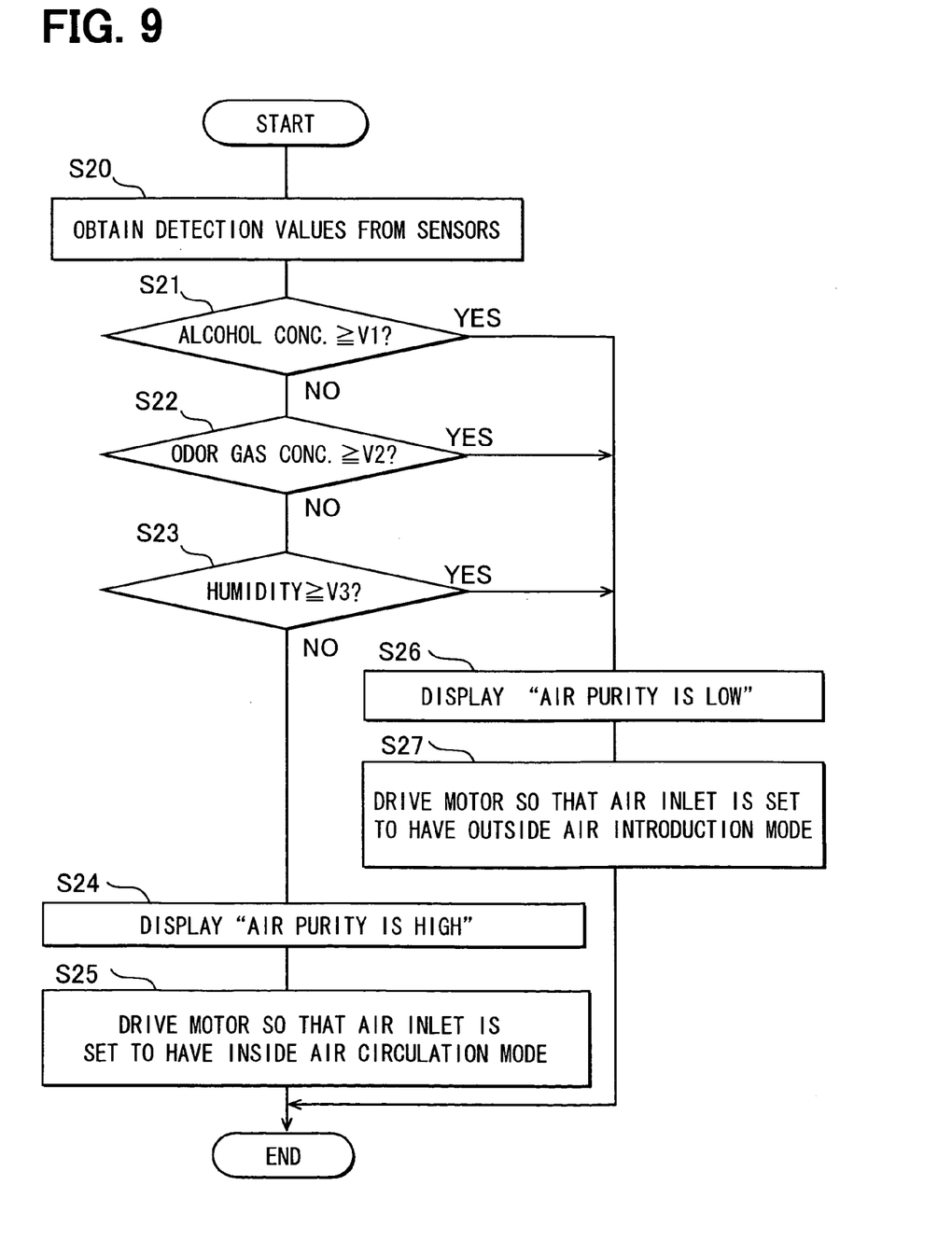
FIG. 9 is a flow chart illustrating an air purity calculation program according to a second embodiment.

Alternatively, the microcomputer 101 of the air-conditioning ECU 100 may correspond to the air purity calculator in a second embodiment. An air purity calculation program of FIG. 9 is memorized in the ROM of the microcomputer 101. The microcomputer 101 will repeat and execute the air purity calculation program.

In the air purity calculation program of FIG. 9, the microcomputer 101 obtains the detection values of the alcohol sensor 17a, the odor sensor 17b, and the humidity sensor 17d from the alcohol-detecting ECU 20 through the multiplex communication line BUS in the process of S20. Process of S21-S27 are approximately the same as that of S11-S17 of FIG. 6, except for the process of S20.

According to the second embodiment, the microcomputer 101 of the air-conditioning ECU 100 automatically switch the air inlet mode into the outside air introduction mode when the air purity in the passenger compartment is low. Therefore, the air purity in the passenger compartment can be made better similarly to the first embodiment.

(Modifications)

The gas sensors 17 are constructed by the alcohol sensor 17a, the odor sensor 17b, the temperature sensor 17c, the humidity sensor 17d, and the oxygen sensor 17e in the first and second embodiments. For example, as shown in a broken line of FIG. 3, an atmospheric pressure sensor 17f to detect an atmospheric pressure in the passenger compartment, and a carbon dioxide sensor 17g to detect a carbon dioxide concentration in the passenger compartment may be provided in addition to the gas sensors 17a-17e. The air state in the passenger compartment can be made more comfortable by monitoring a change of the pressure detected by the sensor 17f and by monitoring a change of the carbon dioxide concentration detected by the sensor 17g.

If the vehicle uses alcohol as fuel, fuel leakage can be prevented by monitoring a change of the alcohol concentration detected by the sensor 17a.

The display 221 connected to the meter ECU 220 corresponds to the alarm portion in the embodiments.

Alternatively, the alarm portion may be a display connected to the navigation ECU 210, a display connected to the air-conditioning ECU 100, or other display mounted in the device 10. Moreover, the alarm portion may be a speaker connected to the navigation ECU 210, or voice message.

The alcohol-detecting ECU 20 and the air-conditioning ECU 100 are configured to cooperate with each other in the first and second embodiments.

Alternatively, a door ECU may further cooperate with the ECUs. For example, the door ECU controls a window motor to open a window when the air purity in the passenger compartment is determined to be low.

The expiration drawing portion may be a pump other than the fan 14. Due to the pump or the fan 14, the air state in the passenger compartment can be efficiently detected. Further, a fan or pump in a conventional device such as the air-conditioning unit, can be eliminated, so that the producing cost can be further reduced.

Such changes and modifications are to be understood as being within the scope of the present invention as defined by the appended claims.

What is claimed is:

1. An alcohol concentration detecting device for a vehicle comprising:
    an alcohol sensor to detect alcohol component contained in an expiration of an occupant of the vehicle;
    a gas sensor to detect gas components other than the alcohol component contained in the expiration; and
    an alcohol-detecting controller to calculate an alcohol concentration of the expiration based on a detection value of the alcohol sensor, wherein
    the alcohol-detecting controller corrects the calculated alcohol concentration based on a detection value of the gas sensor,
    the alcohol sensor and the gas sensor are configured to further detect a state of air in a passenger compartment of the vehicle, and
    the alcohol concentration is calculated when an oxygen concentration in a pas to be detected is lower than a predetermined value, and an air purity is calculated as the state of air in the passenger compartment when the oxygen concentration is equal to or higher than the predetermined value.

2. The alcohol concentration detecting device according to claim 1, further comprising:
    an expiration drawing portion to draw the expiration; and
    an alarm portion to report the state of air in the passenger compartment based on the detection values of the alcohol sensor and the gas sensor, wherein
    the expiration drawing portion draws air in the passenger compartment when the state of air in the passenger compartment is detected.

3. The alcohol concentration detecting device according to claim 1, further comprising:
    a temperature sensor and a humidity sensor, wherein
    the alarm portion reports a temperature and a humidity of air in the passenger compartment as one index of the state of air based on detection values of the temperature sensor and the humidity sensor.

4. The alcohol concentration detecting device according to claim 3, further comprising:
    an odor sensor; and
    an air purity calculator to calculate the air purity in the passenger compartment as one index of the state of air in the passenger compartment, wherein
    the air purity calculator calculates the air purity based on detection values of the alcohol sensor, the humidity sensor and the odor sensor, and
    the alarm portion reports the calculated air purity to the occupant.

5. The alcohol concentration detecting device according to claim 4, further comprising:
    an air-conditioning controller to control air-conditioning of the passenger compartment; and
    an air inlet switching portion to switch an air inlet mode of the air-conditioning, wherein
    the alcohol-detecting controller is connected to the air-conditioning controller through a communication line so that the detection values of the temperature sensor and the humidity sensor are transmitted between the alcohol-detecting controller and the air-conditioning controller, and
    the alcohol-detecting controller sends a control signal to the air-conditioning controller based on the calculated air purity so that the air inlet switching portion is controlled to change the air inlet mode from an inside air circulation mode to an outside air introduction mode.

6. The alcohol concentration detecting device according to claim 4, further comprising:
    an air-conditioning controller to control air-conditioning of the passenger compartment; and
    an air inlet switching portion to switch an air inlet mode of the air-conditioning, wherein
    the alcohol-detecting controller is connected to the air-conditioning controller through a communication line so that the detection values of the temperature sensor, the humidity sensor, the alcohol sensor and the odor sensor are transmitted between the alcohol-detecting controller and the air-conditioning controller, and
    the air-conditioning controller controls the air inlet switching portion based on the calculated air purity so that the air inlet mode is changed from an inside air circulation mode to an outside air introduction mode.

* * * * *